(12) United States Patent
Omi (10) Patent No.: US 9,386,231 B2
(45) Date of Patent: Jul. 5, 2016

(54) STATE MONITORING APPARATUS (71) Applicant: DENSO CORPORATION, Kariya, Aichi-pref. (JP)

(72) Inventor: Takuhiro Omi, Anjo (JP)

(73) Assignee: DENSO CORPORATION, Kariya (JP)

( * ) Notice: Subject to any disclaimer, the term of this patent is extended or adjusted under 35 U.S.C. 154(b) by 0 days.

(21) Appl. No.: 14/421,923

(22) PCT Filed: May 13, 2013

(86) PCT No.: PCT/JP2013/003045
§ 371 (c)(1),
(2) Date: Feb. 16, 2015

(87) PCT Pub. No.: WO2014/054199
PCT Pub. Date: Apr. 10, 2014

(65) Prior Publication Data
US 2015/0237246 A1    Aug. 20, 2015

(30) Foreign Application Priority Data
Oct. 2, 2012 (JP) ................................. 2012-220664

(51) Int. Cl.
*H04N 5/225* (2006.01)
*H04N 5/235* (2006.01)
(Continued)

(52) U.S. Cl.
CPC .......... *H04N 5/2353* (2013.01); *G06K 9/00268* (2013.01); *G06K 9/00845* (2013.01); *G06K 9/4661* (2013.01)

(58) Field of Classification Search
CPC ............ H04N 1/02885; H04N 5/2354; G06K 9/00845; G08B 21/06; B60K 28/02; A61B 5/18

USPC .............................. 348/68, 69, 148, 370, 371; 396/155–206
See application file for complete search history.

(56) References Cited

U.S. PATENT DOCUMENTS

| 2003/0015645 | A1* | 1/2003 | Brickell | ................ | H04N 5/235 |
| | | | | | 250/208.1 |
| 2004/0071458 | A1* | 4/2004 | Motomura | ............ | G03B 15/05 |
| | | | | | 396/159 |

(Continued)

FOREIGN PATENT DOCUMENTS

| JP | H11-109452 A | 4/1999 |
| JP | 2005-151123 A | 6/2005 |

(Continued)

OTHER PUBLICATIONS

International Search Report of the International Searching Authority mailed Jun. 4, 2013 in the corresponding PCT application No. PCT/JP2013/003045 (and English translation).

(Continued)

*Primary Examiner* — Twyler Haskins
*Assistant Examiner* — Dwight C Tejano
(74) *Attorney, Agent, or Firm* — Posz Law Group, PLC (57) ABSTRACT

A state monitoring apparatus in a vehicle monitors the state of a driver using a face image of the driver. The state monitoring apparatus emits light from a light projecting part toward a predetermined area and receives, via an imaging unit, light reflected by the face that is assumed to be positioned in the predetermined area. A control circuit in the state monitoring apparatus adjusts a gradation value of the face image by changing length of an exposure period in which an imaging element of the imaging unit is set to an exposure state. Further, the control circuit controls light emission of the projecting part so that light emission brightness at the time of start of the exposure period becomes higher as the exposure period of the imaging element is shortened.

20 Claims, 8 Drawing Sheets

(51) Int. Cl.
*G06K 9/00* (2006.01)
*G06K 9/46* (2006.01)

(56) References Cited

U.S. PATENT DOCUMENTS

| | | | |
|---|---|---|---|
| 2006/0007346 A1* | 1/2006 | Nakamura | H04N 5/2354 348/362 |
| 2006/0087582 A1* | 4/2006 | Scharenbroch | G06K 9/00604 348/370 |
| 2006/0104488 A1* | 5/2006 | Bazakos | G06K 9/00255 382/118 |
| 2007/0166023 A1 | 7/2007 | Murata | |
| 2008/0084499 A1* | 4/2008 | Kisacanin | A61B 3/113 348/370 |
| 2009/0207301 A1* | 8/2009 | Fransson | H04N 5/232 348/371 |
| 2009/0244288 A1 | 10/2009 | Fujimoto et al. | |
| 2010/0014711 A1* | 1/2010 | Camhi | B60K 28/06 382/104 |
| 2014/0139655 A1* | 5/2014 | Mimar | G08B 21/0476 348/77 |

FOREIGN PATENT DOCUMENTS

| | | |
|---|---|---|
| JP | 2005-338279 A | 12/2005 |
| JP | 2006-209325 A | 8/2006 |
| JP | 2006-311345 A | 11/2006 |
| JP | 2010-215000 A | 9/2010 |
| JP | 2011-142500 A | 7/2011 |

OTHER PUBLICATIONS

Written Opinion of the International Searching Authority mailed Jun. 4, 2013 in the corresponding PCT application No. PCT/JP2013/003045 (and English translation).

Office Action mailed, Sep. 1, 2015 in the corresponding JP application No. 2012-220664 (with English translation).

* cited by examiner

STATE MONITORING APPARATUS

CROSS REFERENCE TO RELATED APPLICATION APPLICATIONS

The present disclosure is a U.S. national stage application of PCT/JP2013/003045 filed on May 13, 2013 and is based on Japanese Patent Application No. 2012-220664 filed on Oct. 2, 2012, the disclosures of which are incorporated herein by reference.

TECHNICAL FIELD

The present disclosure relates to a technique mounted to a vehicle to monitor the state of a manipulator manipulating the vehicle.

BACKGROUND ART

Conventionally, a state monitoring apparatus mounted in a vehicle uses a face image obtained by imaging the face of a manipulator in order to monitor the state of the manipulator. For such capturing of a face image, the state monitoring apparatus includes: a light emitting unit for emitting illumination light toward a predetermined area which is preliminarily specified as an area where the face of the manipulator is positioned; and an imaging unit for capturing an image of the face by receiving light incident from the predetermined area.

Patent literature 1 discloses an imaging apparatus that includes: a flash apparatus having a flash related to the above-described light emitting unit; and an imaging element related to the above-described imaging unit. The imaging apparatus provides a length of an exposure period, in which the imaging element is set to an exposure state, to be constant. According to brightness of a subject to be imaged, the apparatus changes the length of a light emission period of the flash in the exposure period, thereby changing a light emission amount. Further, the change of the light emission amount of the flash results in adjusting a light emission start timing of the flash.

In contrast, the above-described state monitoring apparatus, which is different from the imaging apparatus of the patent literature 1, is permitted to change the length of the exposure period in the imaging unit. Consequently, a gradation value of a face image can be adjusted to lie in a pre-specified range regardless of the intensity of environment light reaching the face of the manipulator. The light emitting unit is controlled so as to continue emission of illumination light in the exposure period.

PRIOR ART LITERATURES

Patent Literature

Patent literature 1: JP 2007-193061 A

SUMMARY OF INVENTION

The inventor of the present disclosure paid attention to light emission of the light emitting unit continued in the exposure period, and examined reduction of heat generation accompanying the light emission. As a result, in cases that the light emission brightness of illumination light from the light emitting unit is lowered to reduce heat generation, it is found that the face image cannot be accurately captured when the environment light reaching the face of the manipulator is strong.

Specifically, the environment light strongly illuminates only a part of the face of the manipulator. This makes it impossible to adjust the entire face image to a proper gradation value by adjusting the length of the exposure period. When the function of the light emitting unit which reduces the influence of the environment light at the time of capturing a face image is not exerted, the imaging unit cannot accurately capture a face image.

An object of the present disclosure is to provide a state monitoring apparatus capable of accurately capturing a face image while reducing heat generation accompanying light emission.

To achieve the above object, according to a first aspect of the present disclosure, a state monitoring apparatus mounted to a vehicle monitors a state of a manipulator manipulating the vehicle by using a face image obtained by imaging face of the manipulator. The apparatus is provided as including the following: an imaging unit generating the face image by receiving light incident from a predetermined area which is preliminarily specified as an area in which the face of the manipulator is positioned; an imaging control section adjusting a gradation value of the face image by changing length of an exposure period in which the imaging unit is set in an exposure state; a light emitting unit continuously emitting illumination light toward the predetermined area in the exposure period which is set by the imaging control section; and a light emission control section controlling the light emitting unit so that light emission brightness at start time of the exposure period becomes higher as the exposure period is shortened by the imaging control section.

According to a second aspect of the present disclosure, a state monitoring method is provided for causing a computer mounted to a vehicle to monitor a state of a manipulator manipulating the vehicle by using a face image obtained by imaging face of the manipulator. The method includes: an imaging step of generating the face image by receiving light incident from a predetermined area which is preliminarily specified as an area in which the face of the manipulator is positioned; an imaging control step of adjusting a gradation value of the face image by changing length of an exposure period in which an exposure state is set in the imaging step; a light emitting step of continuously emitting illumination light toward the predetermined area in the exposure period which is set in the imaging control step; and a light emission control step of controlling the light emitting step so that light emission brightness at start time of the exposure period becomes higher as the exposure period is shortened in the imaging control step.

According to a third aspect of the present disclosure, a non-transitory computer readable storage medium is provided as including instructions for execution by a computer. The instructions include the state monitoring method according to the above second aspect. The method is computer-implemented.

The above-described aspects shorten the exposure period at the time of imaging a face to reduce a gradation value of a face image when environment light reaching the face of a manipulator is strong. Accordingly, light emission brightness of illumination light emitted toward a predetermined range at the time of start of the exposure period is set to be high. This permits the strong illumination light to be continuously emitted to the face of the manipulator, enabling the reduction in the influence of the environment light at the time of capturing a face image.

On the other hand, when the environment light reaching the face of the manipulator is weak, the exposure time at the time of imaging the face is set to be long so as to improve the gradation value of the face image. Accordingly, the light emission brightness of the illumination light emitted toward the predetermined area at the time of start of the exposure period is set to be low. In this case, since the environment light is weak, even when the brightness of illumination light emitted to the face is low, the influence of the environment light to the face image becomes small. Such suppression of the light emission brightness at the time of start of the exposure period can realize the reduction in heat generation accompanying light emission.

The above permits accurate capturing of a face image while certainly reducing heat generation accompanying light emission.

BRIEF DESCRIPTION OF DRAWINGS

The above and other objects, features and advantages of the present disclosure will become more apparent from the following detailed description made with reference to the accompanying drawings. In the drawings.

EMBODIMENTS FOR CARRYING OUT INVENTION

Hereinbelow, a plurality of embodiments of the present disclosure will be described with reference to the drawings. There is a case that, by designating the same reference numeral to corresponding components in the embodiments, repetitive description is omitted. In the case of describing only a part of a component in each embodiment, to the other part of the component, the configuration of another embodiment described earlier can be applied. Components clearly described in each of embodiments can be combined and, in addition, when there is no disturbance in combination, components in a plurality of embodiments can be partly combined even when they are not clearly described. It is assumed that such combination which is not clearly described, of components described in a plurality of embodiments is also disclosed by the following description.

Figure 1:
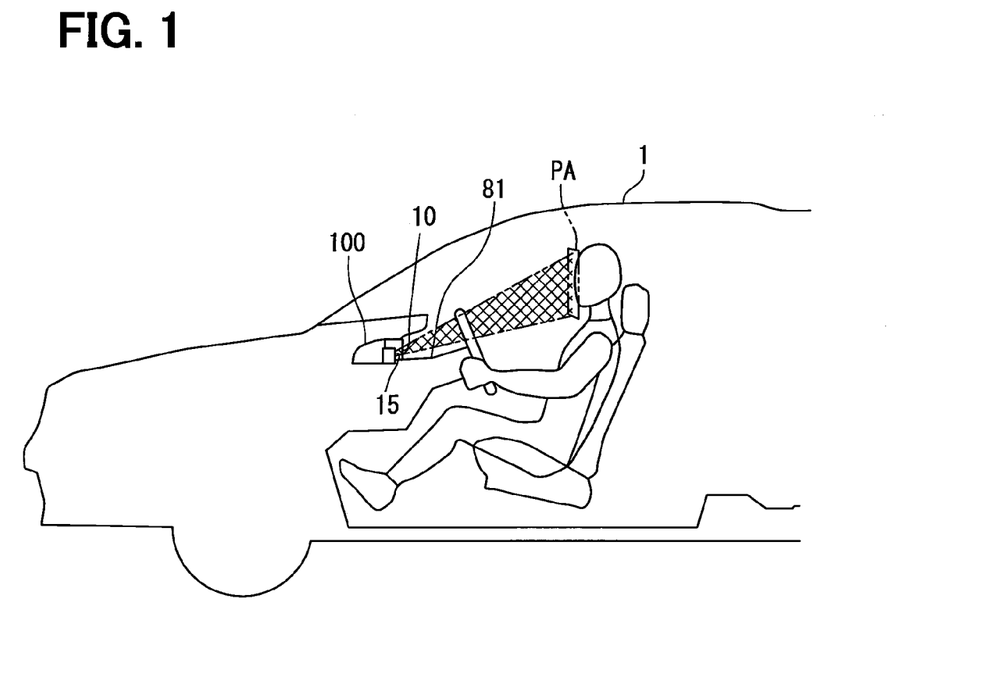
FIG. 1 is a diagram for explaining the disposition in a vehicle, of a state monitoring apparatus according to a first embodiment of the present disclosure.
Figure 2:
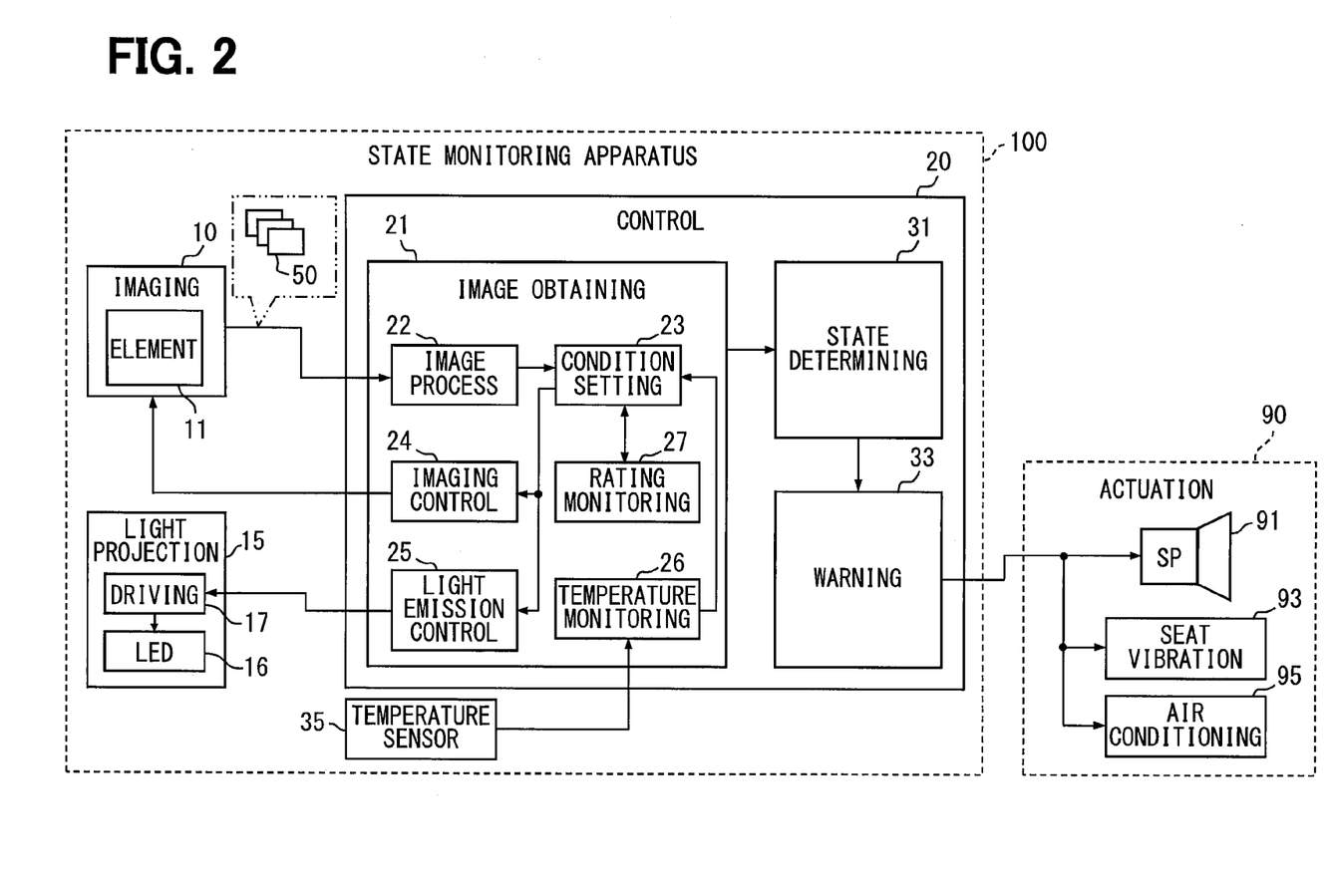
FIG. 2 is a block diagram for explaining electric components of the state monitoring apparatus.

As illustrated in FIG. 1, a state monitoring apparatus 100 according to a first embodiment of the present disclosure is a driver status monitor mounted in a vehicle 1 as a "mobile body" and monitoring the state of a manipulator (hereinbelow, also referred to as a driver) who drives or manipulates the vehicle. As illustrated in FIG. 2, the state monitoring apparatus 100 includes an imaging unit 10, a light projecting part 15, a control circuit 20, and a casing 60 (refer to FIG. 3) housing those components. The state monitoring apparatus 100 is connected to an actuation unit 90 mounted in the vehicle.

Figure 4:
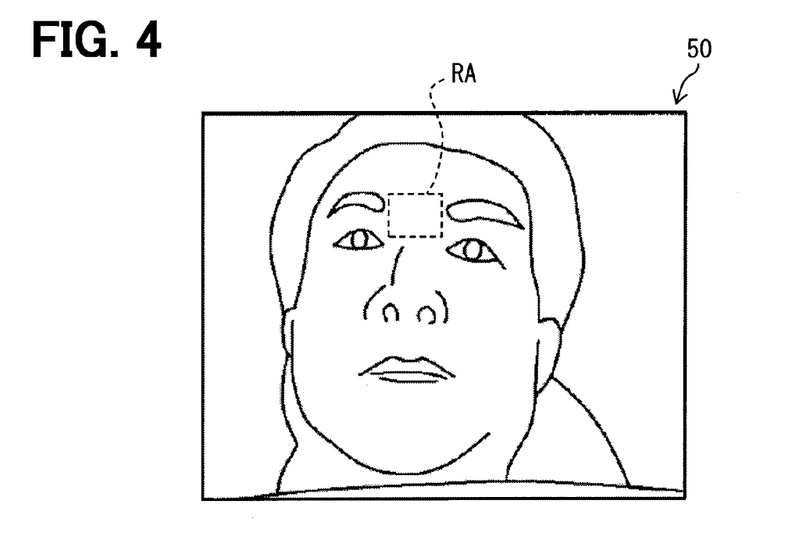
FIG. 4 is a diagram schematically illustrating an example of a face image.

The imaging unit 10 illustrated in FIGS. 1 and 2 generates a face image 51 (refer to also FIG. 4) obtained by imaging the face of the driver in the state monitoring apparatus 100 mounted on the top face of a steering column 81. The imaging unit 10 images a predetermined area PA which is preliminarily specified in the room of the vehicle 1. The predetermined area PA includes an area where the face of a driver seated on the driver's seat is assumed to be positioned. The predetermined area PA is concretely specified on the basis of the eyelips assumed from the eye ranges of the both eyes of the driver and, for example, is specified so as to include 99 percentile of the eyelips.

The imaging unit 10 is a so-called near-infrared camera and is constructed by combining an optical lens and an optical filter to an imaging element 11. The imaging element 11 generates an electric signal according to the intensity of light received by a plurality of pixels arranged along an imaging plane. The imaging element 11 is disposed in a posture that the imaging plane faces toward the predetermined area PA. The imaging element 11 enters an exposure state on the basis of a control signal from the control circuit 20 and, by receiving incident light entering from the predetermined area PA, generates a monochrome face image 50 drawn by gradation of white and black. The face image 50 captured in such a manner is sequentially outputted from the imaging unit 10 toward the control circuit 20.

The light projecting part 15 continuously projects illumination light toward the predetermined area PA during the exposure period of the imaging unit 10. The light projecting part 15 includes a light emitting diode 16 and a driving unit 17. The light emitting diode 16 is provided adjacent to the imaging unit 10 (refer to FIG. 3) and emits illumination light including the near-infrared band. The light emitted from the light emitting diode 16 is projected toward the predetermined area PA and is reflected by the face of the driver toward the imaging unit 10. Consequently, the incident light received by the imaging element 11 includes the light emitted from the light projecting part 15. The driving unit 17 is a circuit which applies predetermined current to the light emitting diode 16. The driving unit 17 switches between the on state and the off state of the current applied to the light emitting diode 16 in accordance with the exposure period of the imaging unit 10 on the basis of the control signal from the control circuit 20. Although a constant current circuit is used as the driving unit 17 in the first embodiment, the driving unit is not limited to a constant current circuit.

The control circuit 20 outputs control signals to the imaging unit 10, the light projecting part 15, and the actuation unit 90, to control the operation of those components. The control circuit 20 is constructed mainly by a microcomputer including a processor performing various arithmetic processes, a RAM functioning as a work area of the arithmetic processes, a flush memory storing a program used for the arithmetic processes. In addition, the control circuit 20 includes a power circuit, which supplies power to the imaging unit 10 and the light projecting part 15.

By executing the preliminarily stored program by the processor, the control circuit 20 includes a plurality of functional blocks such as an image obtaining unit 21, a state determining unit 31, and a warning control unit 33. The functional blocks are also called functional sections.

The image obtaining unit 21 is a functional block performing face recognition of the driver by using the face image 50. The image obtaining unit 21 sets imaging conditions in the imaging unit 10 and light emitting conditions in the light projecting part 15 to obtain the face image 50 from which the face of the driver can be extracted. The image obtaining unit 21 outputs control signals to the imaging unit 10 and the light projecting part 15 to make the imaging unit 10 and the light projecting part 15 execute operations according to the imaging conditions and the light emitting conditions which are set. The image obtaining unit 21 obtains the face image 50 captured as described above from the imaging unit 10. The image obtaining unit 21 computes values related to the orientation of the face of the driver and the degree of opening of each of the eyes (hereinbelow, called "opening eye degree") and values related to the degree of sleepiness of the driver by an image process on the obtained face image 50.

The state determining unit 31 compares a value computed by the image obtaining unit 21 with a preset threshold. By the comparing process, the state determining unit 31 estimates, for example, whether a sign of inattentive driving or a sign of drowsy driving is detected or not. The state determining unit 31 which detects any of the above-described signs determines occurrence of a state that a warning has to be given to the driver.

The warning control unit 33 is connected to the actuation unit 90. By performing a warning process when the state determining unit 31 determines occurrence of the state that a warning has to be given to the driver, the warning control unit 33 outputs a control signal to the actuation unit 90. The warning control unit 33 makes the actuation unit 90 operate, thereby giving a warning to the driver.

Figure 3:
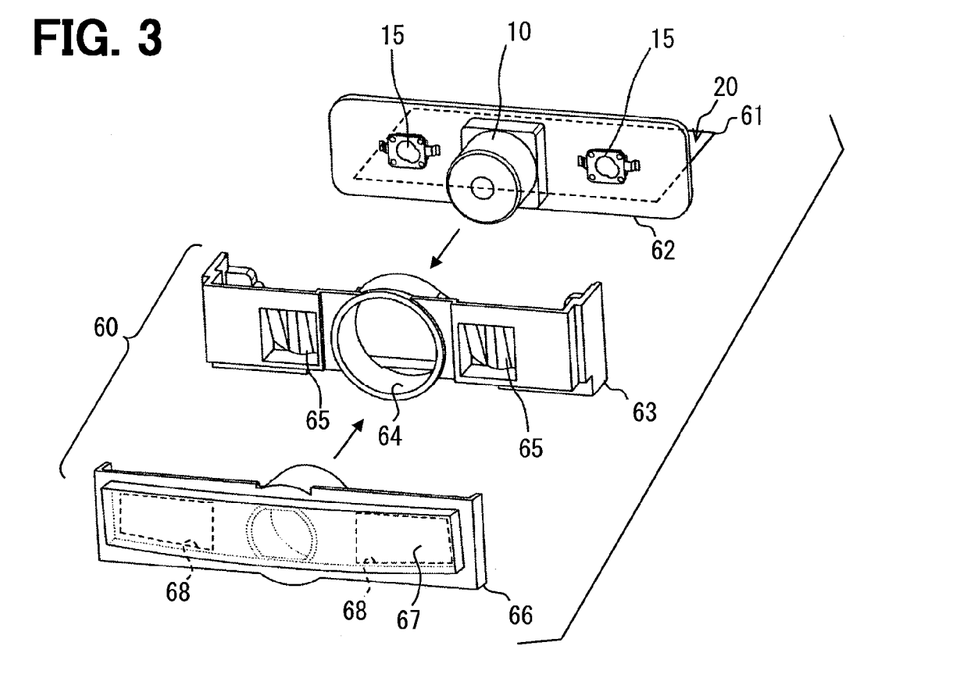
FIG. 3 is a perspective view for explaining mechanical components of the state monitoring apparatus.

The casing 60 includes, as illustrated in FIG. 3, a body member 63, a front cover member 66, and a not-illustrated rear cover member.

The body member 63 holds a sub substrate 62 on which the light projecting parts 15 and the imaging unit 10 are mounted. A main substrate 61 in which the control circuit 20 is formed is attached to the sub substrate 62 in a posture that it is orthogonal to the sub substrate 62. In the body member 63, an insertion hole 64 and light distribution parts 65 are provided. The insertion hole 64 is provided in the center portion in the horizontal direction of the body member 63. The imaging unit 10 mounted on the sub substrate 62 is inserted in the insertion hole 64. The insertion hole 64 cooperates with a hole for light shielding formed in the sub substrate 62 to exert a light shielding function between the light projecting parts 15 and the imaging unit 10, thereby preventing light leakage from the light projecting parts 15 to the imaging unit 10. The light distribution parts 65 are disposed so as to sandwich the insertion hole 64 in the horizontal direction and are opposed to the light projecting parts 15 mounted on the sub substrate 62. The light distribution parts 65 distribute light to the predetermined area PA (refer to FIG. 1) while transmitting light emitted from the light projecting parts 15.

The front cover member 66 is provided with a visible light filter 67. The visible light filter 67 transmits mainly light from red to the near-infrared band used for generation of the face image 50 (refer to FIG. 4) and blocks light in the visible light range which is unnecessary for generation of the face image 50. The visible light filter 67 covers openings 68 formed in positions opposed to the light distribution parts 65 in the front cover member 66. The rear cover member is disposed on the side opposite to the front cover member 66 while sandwiching the body member 63. The rear cover member covers the substrates 61 and 62 to protect them from dust and dirt in the atmosphere.

The actuation unit 90 illustrated in FIG. 2 includes, for example, a speaker 91, a seat vibrating apparatus 93, and an air conditioning apparatus 95 mounted in the vehicle 1 (refer to FIG. 1). The speaker 91 draws the driver's attention by reproducing sound data on the basis of a control signal from the warning control unit 33. The seat vibrating apparatus 93 is installed in the seating face of the driver's seat and draws the driver's attention by vibrating the driver's seat on the basis of a control signal from the warning control unit 33. The air conditioning apparatus 95 draws the driver's attention by an operation such as introduction of outside air into the room of the vehicle 1 on the basis of a control signal from the warning control unit 33.

Next, the details of the control of the light projecting part 15 executed by the image obtaining unit 21 will be described. The image obtaining unit 21 includes, as sub functional blocks, an image processing block 22, a temperature monitoring block 26, a condition setting block 23, a rating monitoring block 27, an imaging control block 24, and a light emission control block 25.

The image processing block 22 obtains the face image 50 captured on the basis of a control signal from the imaging control block 24 from the imaging unit 10. The image processing block 22 sets, for example, a glabella (a region between eyebrows) of the driver as a recognition target area (RA) (refer to FIG. 4). While following the recognition target area RA, the image processing block 22 extracts the brightness, that is, a gradation value of the recognition target area RA.

The temperature monitoring block 26 is connected to a temperature sensor 35. The temperature sensor 35 is provided in the state monitoring apparatus 100 and detects the apparatus temperature of the apparatus 100. The temperature monitoring block 26 obtains the apparatus temperature detected by the temperature sensor 35.

The condition setting block 23 performs a control for adjusting a gradation value extracted by the image processing block 22. Concretely, the condition setting block 23 sets imaging conditions in the imaging unit 10 on the basis of a preset control table so that the face image 50 having excellent contrast is captured in response to an exposure instruction from the image obtaining unit 21. As the imaging conditions, the condition setting block 23 changes, for example, a gain value, exposure time, and an exposure timing.

Figure 5:
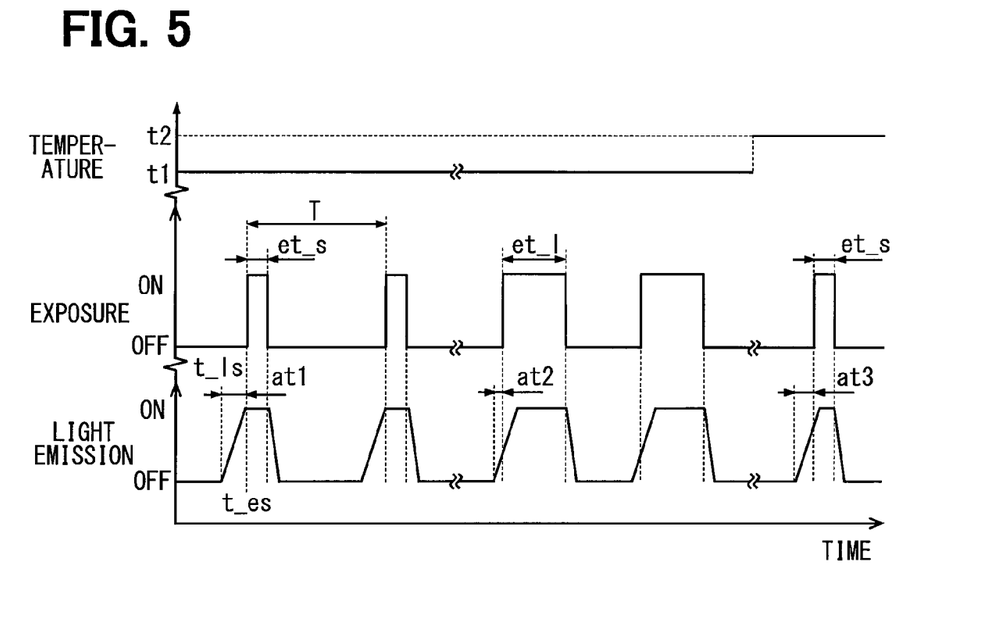
FIG. 5 is a time chart illustrating transition of an apparatus temperature, an exposure state, and a light emission state.

The gain value is the ratio of an input and an output at the time of amplifying a signal output from the imaging element 11 and outputting the amplified signal. The gain value is maintained at an almost constant value even when the gradation value of the recognition target area RA fluctuates or slightly increases as the gradation value of the recognition target area RA decreases (the area becomes darker). The exposure time is, as illustrated in FIG. 5, the length of the exposure period in which the exposure state is maintained in one image capture. The exposure time is set longer as the gradation value of the recognition target area RA decreases. Therefore, as illustrated in FIG. 5, the length et_s of the exposure period under an environment of a large amount of environment light is set shorter than the length et_l of the exposure period under an environment of a small amount of environment light. The exposure timing instructs the start time t_es of the exposure period so that imaging is performed in a cycle T.

The imaging unit 10 (refer to FIG. 2) can properly change the cycle T of imaging in an imaging mode (snapshot mode) of continuously capturing the face image 50. For example, when the cycle T is set to about 33 milliseconds, imaging of the face image 50 is executed at 30 frames per second. The exposure timing is associated with the light emission timing which will be described later.

Figure 6:
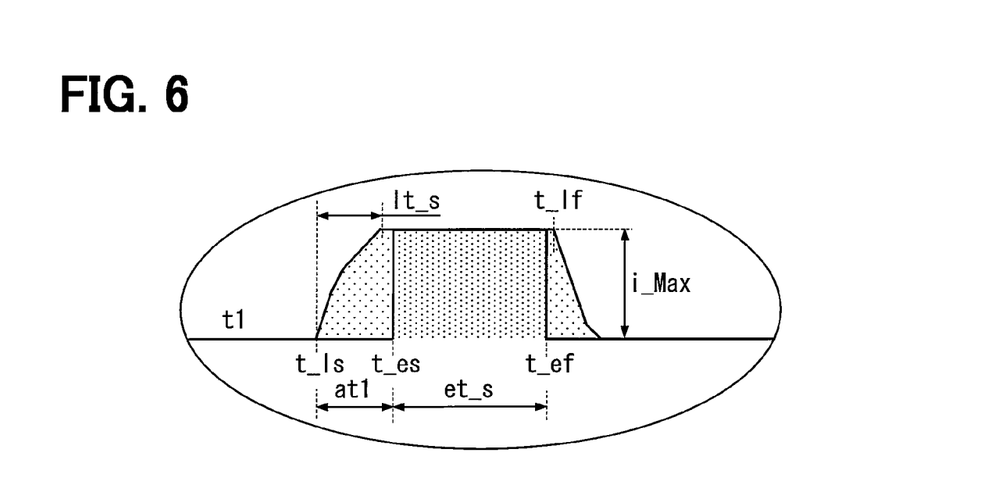
FIG. 6 is a diagram in which the waveform illustrating a light emission state is overlapped with the waveform illustrating an exposure state.

In addition, the condition setting block 23 illustrated in FIG. 2 sets light emission conditions in accordance with the imaging conditions. As the light emission conditions, the condition setting block 23 changes, for example, light emission time and light emission timing. The light emission brightness of the light emitting diode 16 (refer to FIG. 2) in the first embodiment is maintained at maximum brightness from the start time t_es to the end time t_ef of the exposure period, so as to be equal to or higher than light emission brightness at the start time t_es of the period, as shown in FIG. 6.

The light emission time is length of the light emission period in which the light emission state is maintained during one image capture. The light emission time changes according to the exposure time and is set so as to be longer than the exposure time. The light emission timing instructs the start time t_ls of the light emission period. The start time t_ls of the light emission period in which the light emitting diode 16 is in the light emission state is set to be in precedence to the start time t_es of the exposure period. A period in which the start time t_ls of the light emission period is in precedence to the start time t_es of the exposure period (hereinbelow, called "precedence period") is set to be longer as the exposure period is set shorter. Therefore, the length at1 of the precedence period for the length of the exposure period being et_s is assured to be longer than the length at2 of the precedence period for the length of the exposure period being et_l. Consequently, as the exposure period becomes shorter, the light emission brightness of the light emitting diode 16 at the start time t_es of the exposure period becomes higher. Concretely, while the light emission brightness at the start time t_es of the exposure period for the precedence period being at1 is equivalent (100%) to the maximum brightness, the light emission brightness for the precedence period being at2 is about 30% of the maximum brightness.

The precedence period is adjusted between, for example, 0 to about 100 microseconds. Such values related to the light emission timing are desirably set in consideration of the time constant in the circuit of the light projecting part 15 and rise time of current required when the light emission of the light emitting diode 16 shifts from an off state to an on state. The waveform indicating the light emission state in FIG. 5 shows the value of current actually flowing in the light emitting diode 16.

The condition setting block 23 illustrated in FIG. 2 sets a light emission condition, concretely, a precedence period which is provided at the light emission timing on the basis of the apparatus temperature obtained by the temperature monitoring block 26. The precedence period is set shorter as the apparatus temperature becomes higher as illustrated in FIG. 5. Therefore, the length at3 of the precedence period for the environment temperature being T2 is set shorter than the length at1 of the precedence period for the environment temperature being T1, T1 being lower than T2. By the setting, the light emission brightness of the light emitting diode 16 at the start time t_es of the exposure period becomes lower as the apparatus temperature becomes higher. Concretely, the light emission brightness for the precedence period being at3 is about 90% of the maximum brightness.

The rating monitoring block 27 illustrated in FIG. 2 stores a rating condition of the light emitting diode 16. Specifically, the light emitting diode 16 specifies, as the rating condition, the maximum value of the on-duty ratio corresponding to the cycle T and the current value. The rating monitoring block 27 monitors whether the on-duty ratio determined by the light emission timing and light emission time satisfies the rating condition or not with respect to the light emission condition set by the condition setting block 23. When the light emission condition set by the condition setting block 23 exceeds the rating condition, the rating monitoring block 27 changes the light emission condition to a value which does not exceed the rating condition in order to prevent damage of the light emitting diode 16.

The imaging control block 24 generates a control signal based on a control value computed by the condition setting block 23 and outputs it to the imaging unit 10. The control value used in the imaging control block 24 is a value according to the imaging conditions set by the condition setting block 23. The light emission control block 25 generates a control signal based on a control value computed by the condition setting block 23 and outputs it to the light projecting part 15. The control value used in the light emission control block 25 is a value according to the light emission conditions set by the condition setting block 23.

Figure 7:
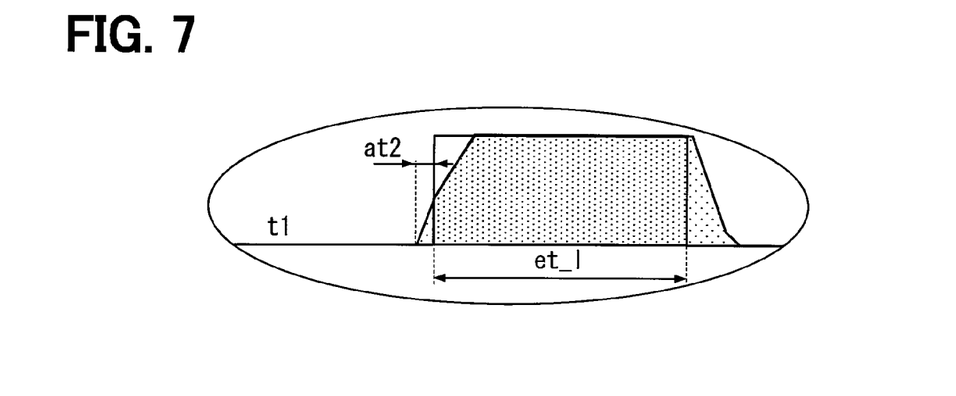
FIG. 7 is a diagram in which the waveform illustrating a light emission state is overlapped with the waveform illustrating an exposure state.
Figure 8:
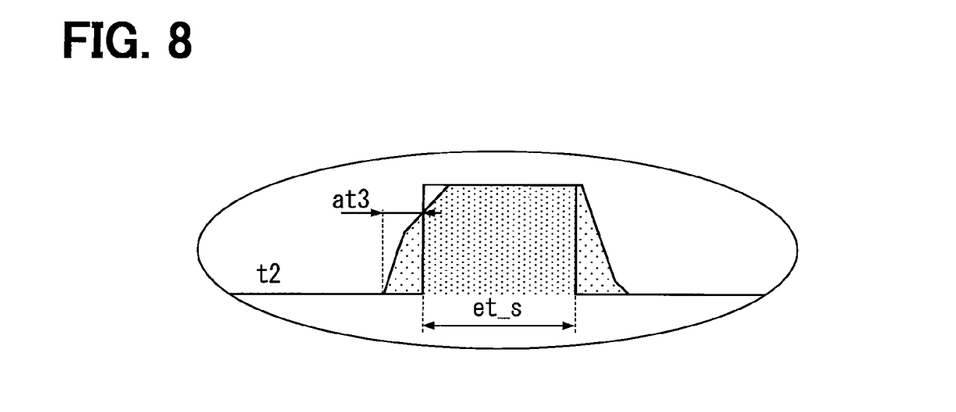
FIG. 8 is a diagram in which the waveform illustrating a light emission state is overlapped with the waveform illustrating an exposure state.

The details of the light emission control described above will be more specifically described with reference to FIGS. 6 to 8. In FIGS. 6 to 8, the waveform of a time chart indicating the light emission state is overlapped with the waveform of a time chart indicating the exposure state. In addition, the positions indicating the on state and the off state of the waveform expressing the light emission state are aligned with the positions indicating the on state and the off state of the waveform expressing the exposure state. The shape of each of the waveforms in FIGS. 6 to 8 is obtained by enlarging the shape of each of the waveforms in FIG. 5 in the direction of the time axis.

A value obtained by dividing the area obtained by time integration in the exposure period in the waveform expressing the light emission state (refer to the dark dotted area in FIGS. 6 to 8) by the area obtained by the time integration in the exposure period in the waveform expressing the exposure state is defined as an illumination cover ratio. As will be described later, the illumination cover ratio changes according to the exposure period and the apparatus temperature.

FIG. 6 is a diagram illustrating the waveforms overlapped when the length of the exposure period is et_s and the apparatus temperature is t1. In this case, the precedence period at1 is assured to be long, so that the light emission brightness of the light emitting diode 16 (refer to FIG. 2) reaches the maximum brightness before the start time t_es of the exposure period. Therefore, the entire area expressing the on state of the exposure state is covered by the area expressing the on state of the light emission state. Therefore, the illumination cover ratio is substantially 100%.

FIG. 7 is a diagram illustrating the waveforms overlapped when the length of the exposure period is et_t and the apparatus temperature is t1. In this case, the precedence period at2 is shorter than the above-described precedence period at1 (refer to FIG. 6), so that the light emission brightness of the light emitting diode 16 (refer to FIG. 2) reaches the maximum brightness after the start time of the exposure period. Therefore, a part of the area expressing the on state of the exposure state lies out of the area expressing the on state of the light emission state. As a result, the illumination cover ratio is, for example, about 95%.

FIG. 8 is a diagram illustrating the waveforms overlapped when the length of the exposure period is et_s and the apparatus temperature is t2. In this case, the precedence period at3 is shorter than the above-described precedence period at1 (refer to FIG. 6), so that the light emission brightness of the light emitting diode 16 (refer to FIG. 2) reaches the maximum brightness after the start time of the exposure period. Therefore, a part of the area expressing the on state of the exposure state lies out of the area expressing the on state of the light emission state, and the illumination cover ratio is, for example, about 90%.

As obvious from the above description, light emission of the light projecting parts 15 illustrated in FIG. 2 is controlled so that the illumination cover ratio becomes higher as the exposure period is set shorter. In addition, the light emission of the light projecting parts 15 is controlled so that the illumination cover ratio becomes lower as the apparatus temperature becomes higher.

Figure 9:
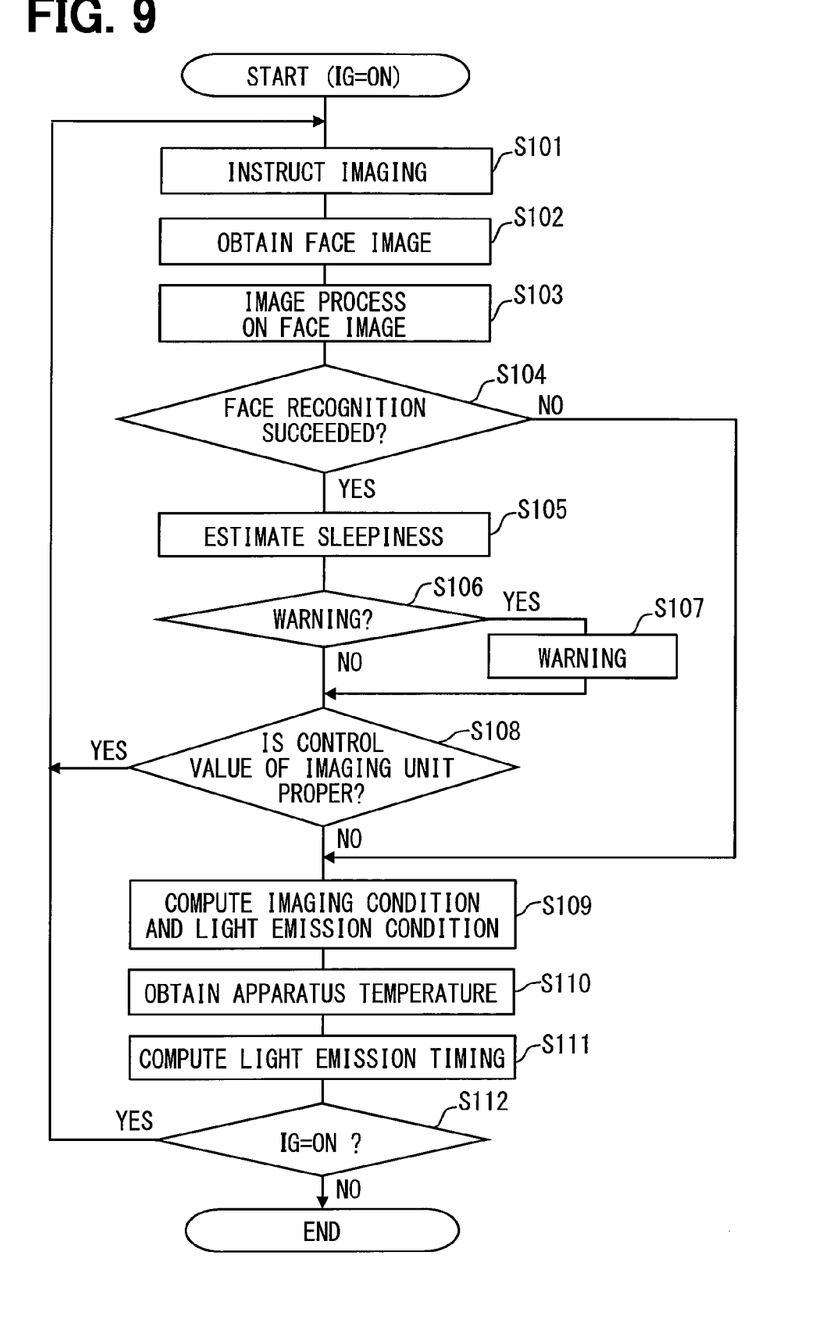
FIG. 9 is a flowchart illustrating processes executed by an image obtaining unit.

Next, the processes executed by the image obtaining unit 21 to realize the light emission control associated with the imaging control as described above will be described specifically with reference to FIG. 9. The processes illustrated in FIG. 9 are started by the image obtaining unit 21 when the ignition of the vehicle 1 (refer to FIG. 1) is set to the on state.

It is noted that a flowchart or the processing of the flowchart in the present application includes sections (also referred to as steps), each of which is represented, for instance, as S101. Further, each section can be divided into several sub-sections while several sections can be combined into a single section. Furthermore, each of thus configured sections can be also referred to as a device, module, or means.

In S101, the control values of the imaging unit 10 and the light projecting unit 15 used for control by the light emission control block 25 and the imaging control block 24 are set. In S101 of the first time after the ignition is set to the on state, a preliminarily specified default value is used. On the other hand, in S101 of the second and subsequent times, control values computed in S109 and S111 of last time are used. Capture of the face image 50 is instructed by the control signals output from the control blocks 24 and 25, and the routine advances to S102. By the process of S101, the light projecting parts 15 emit illumination light, and the imaging unit 10 generates the face image 50 and outputs it to the image processing block 22.

In S102, the face image 50 captured on the basis of the instruction of S101 is obtained, and the routine advances to S103. In S103, an image process on the face image 50 obtained in S102 is executed, and the routine advances to S104. In S104, whether face recognition of the driver succeeded in the image process in S103 or not is determined. When it is determined in S104 that the face recognition was not successful, the routine advances to S109. On the other hand, when it is determined in S104 that the face recognition was successful, the routine advances to S105.

In S105, on the basis of the result of the image process executed in S103, the orientation of the face of the driver, and the eye opening degree are detected, and the degree of sleepiness of the driver is estimated. The orientation of the face, the eye opening degree, and the degree of sleepiness are digitized so as to be quantitatively evaluated, and the routine advances to S106.

In S106, by comparing the value computed in S105 with a preset threshold, the presence or absence of a value at which warning has to be sent is determined. When there is a value at which warning has to be sent in S106 and it is determined that a sign of inattentive driving or a sign of drowsy driving is detected, the routine advances to S107. In S107, a warning process for making the actuation unit 90 operate is executed, and the routine advances to S108. On the other hand, when it is determined in S106 that there is no value at which warning has to be sent, the routine advances to S108.

In S108, whether the control value of the imaging unit 10 set in S101 is proper or not is determined. Concretely, whether the gradation value of the above-described recognition target area RA (refer to FIG. 4) lies in a proper range or not is determined. When it is determined in S108 that the control value of the imaging unit 10 is proper, the routine returns to S101. On the other hand, when it is determined in S108 that the control value of the imaging unit 10 is not proper, the routine advances to S109.

In S109 based on the negative determination in S104 and the negative determination in S108, the imaging condition and the light emission condition at the time of capturing the next frame are computed. That is, the control values of the light projecting part 15 and the imaging unit 10 are determined so that the gradation value of the above-described recognition target area RA lies in a proper range.

In S110 subsequent to S109, the apparatus temperature detected by the temperature sensor 35 is obtained. After that, the routine advances to S111. In S111, based on the exposure period in the imaging conditions computed in S109 and the apparatus temperature obtained in S111, a precedence period is determined. From the determined precedence period, the light emission timing (the start time t_ls of the light emission period) is computed. The control values determined in S109 and S111 are set in the light emission control block 25 and the imaging control block 24 in S101 of next time and reflected in the imaging of the face image 50.

In S112 subsequent to S111, whether the on state of ignition of the vehicle 1 is continued or not is determined. When the negative determination is made in S112 since ignition is set to the off state, the process is finished. On the other hand, when positive determination is made in S112, the routine returns to S101.

According to the first embodiment described above, when the exposure period is set short in the case where environment light reaching the face of the driver is strong, the light emission brightness of the illumination light emitted at the start time t_es of the exposure period is set high. This can reduce the influence of the environment light at the time of imaging of the face image 50, avoiding the situation that only a part of the face of the driver is strongly illuminated by the environment light to disable capturing of the face image 50 in proper contrast.

On the other hand, when the exposure time is made long in the case where the environment light reaching the face of the driver is weak, the light emission brightness of the illumination light emitted at the start time t_es of the exposure period is made low. In this case, since the environment light is weak, even when the brightness of the illumination light emitted to the face is low, the influence of the environment light to the face image 50 can be made small. Thus suppressing of the light emission brightness at the start time t_es of the exposure period to be low can realize the reduction in the light generation of the light projecting parts 15 accompanying the light emission.

Therefore, after the heat generation and consumption energy accompanying the light emission is reduced, the face image 50 can be accurately captured.

In addition, according to the first embodiment, from the start time t_es to the end time t_ef of the exposure period, the light emission brightness of the illumination light is maintained high. By emitting strong illumination light to the face of the driver in the entire exposure period, the effect of reducing the influence of the environment light at the time of imaging the face image 50 is exhibited with higher probability.

In the first embodiment, making the precedence period long assures the high light emission brightness at the start time t_es of the exposure period. In such a mode, a transition period of making light emission of the light emitting diode 16 shift from the off state to the on state (refer to the rise time It_s of current in FIG. 6) can be assured to be long. This can realize the operation of making the light emission brightness high at the start time t_es of the exposure period while suppressing electric noise which occurs at the time of switching the on state and off state of the light emitting diode 16.

Further, the life by cumulative lighting time of the light emitting diode 16 according to the first embodiment becomes a factor of considerably shortening the life including the driving unit 17 when the operation under high-temperature environment is continued. Therefore, by suppressing the light emission brightness at the start time t_es of the exposure period as the apparatus temperature increases, the state monitoring apparatus 100 lessens the load of the light emitting diode 16 and the driving unit 17. Such a control allowing decrease in the light emission brightness at the start time t_es of the exposure period can realize the reliably operation in the long period of the light projecting parts 15.

In the first embodiment, the vehicle 1 is referred to as a mobile body, the imaging unit 10 is referred to as an imaging device or an imaging means, and the light projecting part 15 is also referred to as a light emitting part, a light emitting device, or a light emitting means. The condition setting block 23 and the imaging control block 24 cooperate to function as an imaging control unit and are also referred to as an imaging control device or an imaging control means. The condition setting block 23 and the light emission control block 25 cooperate to function as a light emission control unit and are also referred to as a light emission control device or a light emission control means. The temperature sensor 35 is also referred to as a temperature detecting unit, a temperature detecting device, or a temperature detecting means. S101 is called an imaging section or an imaging step and a light emission section or a light emission step. S109 is also referred to as an imaging control section or an imaging control step. S111 is also referred to as a light emission control section or a light emission control step.

Second Embodiment

Figure 10:
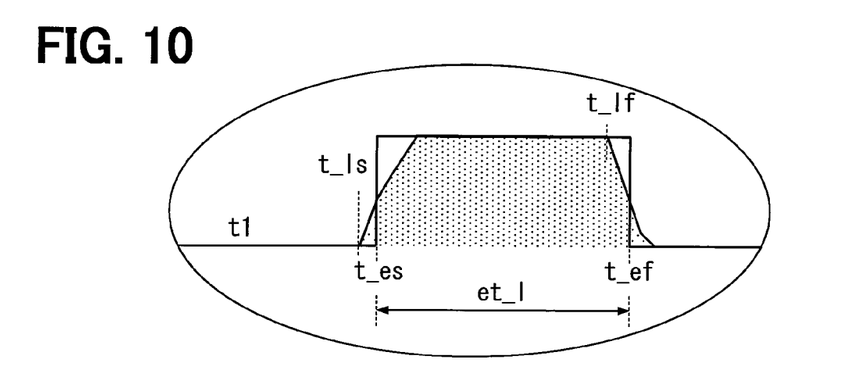
FIG. 10 is a diagram illustrating a modification of FIG. 7.
Figure 11:
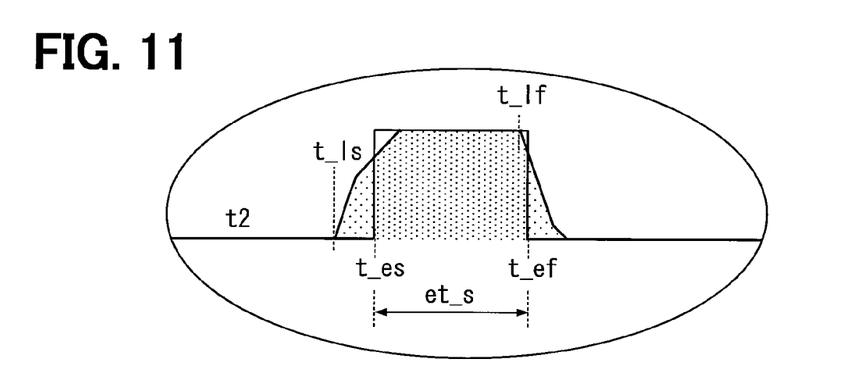
FIG. 11 is a diagram illustrating a modification of FIG. 8.

A second embodiment of the present disclosure illustrated in FIGS. 10 and 11 is a modification of the first embodiment. In the second embodiment, with respect to a transition period at the time of lights-out of making the light emission state shift from the on state to the off state, the fall start time (hereinbelow, called "lights-out time") t_lf for the end time t_ef of the exposure period is changed according to the length of the exposure period and the apparatus temperature. Hereinbelow, while comparing FIGS. 10 and 11 with FIG. 6, the details of the light emission control executed in the second embodiment will be described.

In the second embodiment, when the length of the exposure period is et_s and the apparatus temperature is t1, like in the first embodiment illustrated in FIG. 6, the lights-out time t_lf is specified after end of the exposure period. Consequently, the light emitting diode 16 (refer to FIG. 2) maintains the maximum brightness until the end time t_ef of the exposure period, so that the illumination cover ratio is 100% like in the first embodiment.

FIG. 10 is a diagram illustrating the waveforms overlapped when the length of the exposure period is et_l and the apparatus temperature is t1. In this case, the lights-out time t_lf is specified prior to the end time t_ef of the exposure period. Therefore, the light emission brightness at the end time t_ef of the exposure period becomes, for example, about 30% of the maximum brightness like the light emission brightness at the start time t_es of the exposure period. As a result, the illumination cover ratio becomes about 90%.

FIG. 11 is a diagram illustrating the waveforms overlapped when the length of the exposure period is et_s and the apparatus temperature is t2. In this case, the lights-out time t_lf is specified prior to the end time t_ef of the exposure period. Therefore, the light emission brightness at the end time t_ef of the exposure period becomes, for example, about 90% of the maximum brightness. As a result, the illumination cover ratio becomes about 85%.

As obvious from the above description, light emission of the light projecting parts 15 of the second embodiment (refer to FIG. 2) is controlled so that the light emission brightness at the end time t_ef of the exposure period becomes higher as the exposure period is set shorter. Therefore, in a manner similar to the first embodiment, the illumination cover ratio becomes higher as the exposure period becomes shorter. Consequently, also in the state monitoring apparatus according to the second embodiment, the remarkable effect can be realized such that when the environment light is strong, the face image 50 (refer to FIG. 4) is accurately captured by irradiation of strong illumination light and, when the environment light is weak, light generation is reduced by suppressing light emission.

In addition, light emission of the light projecting parts 15 of the second embodiment (refer to FIG. 2) is controlled so that the light emission brightness at the end time t_ef of the exposure period decreases as the apparatus temperature becomes higher. As described above, the execution of the control which lessens the load of the light emitting diode 16 (refer to FIG. 2) and the driving unit 17 (refer to FIG. 2) when the apparatus temperature is high can realize reliable operation of the light projecting parts 15 for long time in a manner similar to the first embodiment.

Also in the second embodiment, by controlling the lights-out time t_lf in addition to the light emission time (t_ls), the illumination cover ratio according to the length of the exposure period can be flexibly changed. Therefore, while accurately capturing the face image 50 (refer to FIG. 4), realization of the light emission control and the imaging control for reducing light generation is further increased.

Third Embodiment

Figure 12:
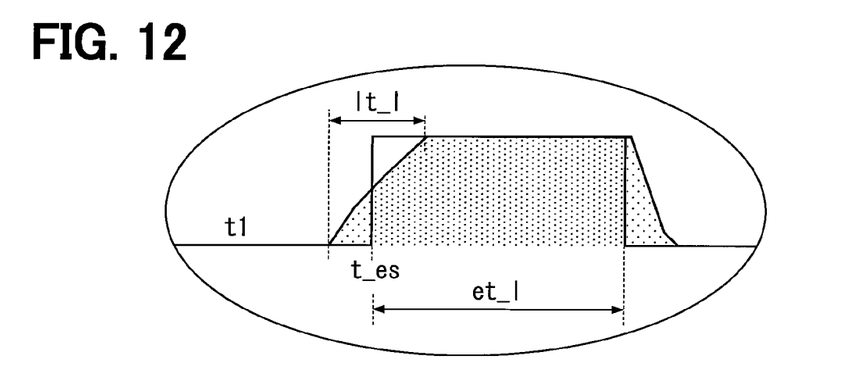
FIG. 12 is a diagram illustrating another modification of FIG. 7.
Figure 13:
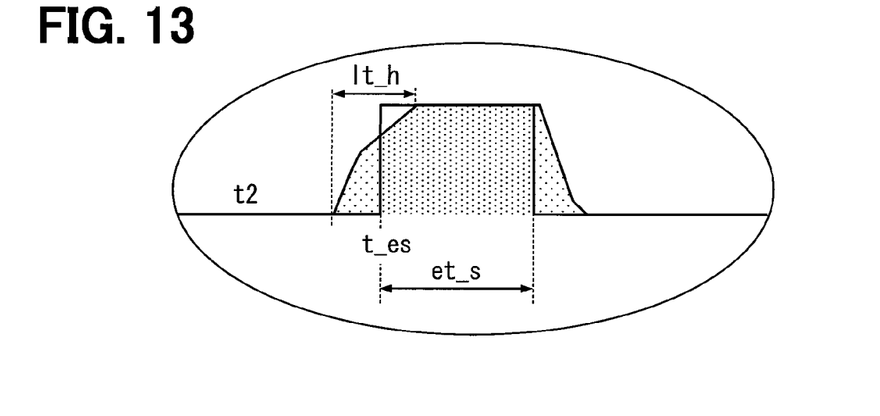
FIG. 13 is a diagram illustrating another modification of FIG. 8.

A third embodiment of the present disclosure illustrated in FIGS. 12 and 13 is another modification of the first embodiment. In the third embodiment, the transition period at the time of lights-on of making the light emission state of the light emitting diode 16 shift from the off state to the on state, that is, the rise time of current by the driving of the driving unit 17 is positively controlled according to the length of the exposure period and the apparatus temperature. Hereinbelow, while comparing FIGS. 12 and 13 with FIG. 6, the details of the light emission control executed in the third embodiment will be described.

FIG. 12 is a diagram illustrating the waveforms overlapped when the length of the exposure period is et_l and the apparatus temperature is t1. The current rise time It_l in this case is controlled to be longer than the current rise time It_s (refer to FIG. 6) in the case where the length of the exposure period is et_l. Such a control makes the light emission brightness at the start time t_es of the exposure period become about 30% of the maximum brightness.

FIG. 13 is a diagram illustrating the waveforms overlapped when the length of the exposure period is et_s and the apparatus temperature is t2. The current rise time It_h in this case is controlled to be longer than the current rise time It_s (refer to FIG. 6) in the case where the apparatus temperature is t2. Such a control makes the light emission brightness at the start time t_es of the exposure period become about 90% of the maximum brightness.

As obvious from the above description, in the light projecting parts 15 (refer to FIG. 2) of the third embodiment, as the exposure period is shortened, the precedence period is made longer and the current rise time is shortened. This controls the light emission of the light projecting parts 15 to permit the light emission brightness at the start time t_es of the exposure period to become higher. The state monitoring apparatus according to the third embodiment can also realize the remarkable effect such that: when the environment light is strong, the face image 50 is accurately captured by irradiation of strong illumination light; when the environment light is weak, light generation is reduced by suppressing light emission.

In addition, light emission of the light projecting parts 15 (refer to FIG. 2) of the third embodiment is controlled so that the light emission brightness at the start time t_es of the exposure period decreases as the apparatus temperature becomes higher. As described above, the execution of the control which lessens the load of the light emitting diode 16 and the driving unit 17 when the apparatus temperature is high can realize reliable operation of the light projecting parts 15 for long time in a manner similar to the first embodiment.

Further, in the third embodiment, when the exposure period is long, long current rise time is assured. Therefore, occurrence of electric noise accompanying switching operation of the light emitting diode 16 is suppressed. In addition, when the exposure period is short, the light emission period can be shortened by shortening the current rise time. This further improves the effect of reducing heat generation accompanying light emission.

Other Embodiments

Although the plurality of embodiments of the present disclosure have been described above, the disclosure is not interpreted with limit to the foregoing embodiments but can be applied to various embodiments and combinations without departing from the gist of the present disclosure.

Figure 14:
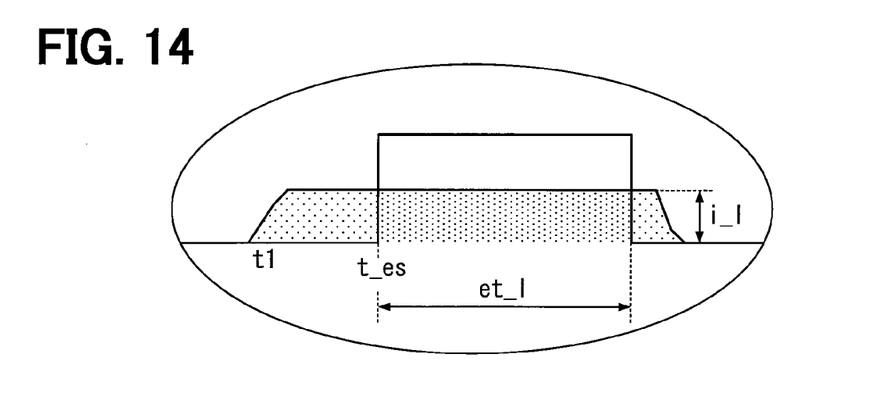
FIG. 14 is a diagram illustrating further another modification of FIG. 7.

A first modification of the embodiments employs a driving unit capable of changing the value of current applied to the light emitting diode 16. Consequently, when the length of the exposure period is et_l as illustrated in FIG. 14, the maximum i_l of the value of current applied to the light emitting diode 16 is controlled to be lower than the maximum current value i_Max (refer to FIG. 6) applied when the length of the exposure period is et_s. Also by such a control, the light emission brightness at the start time t_es of the exposure period can be set to about 30% of the maximum brightness.

In the modification of the embodiments, the light emission brightness at the end time t_ef of the exposure period is set lower than the light emission brightness at the start time t_es of the exposure period.

In the foregoing embodiments, the current value determining the light emission brightness shifts constant after it becomes maximum during the period from the start time t_es of the exposure period to the end time t_ef of the exposure period. However, the current value may slightly fluctuate in the exposure period and become lower than, for example, the current value at the start time t_es of the exposure period.

Figure 15:
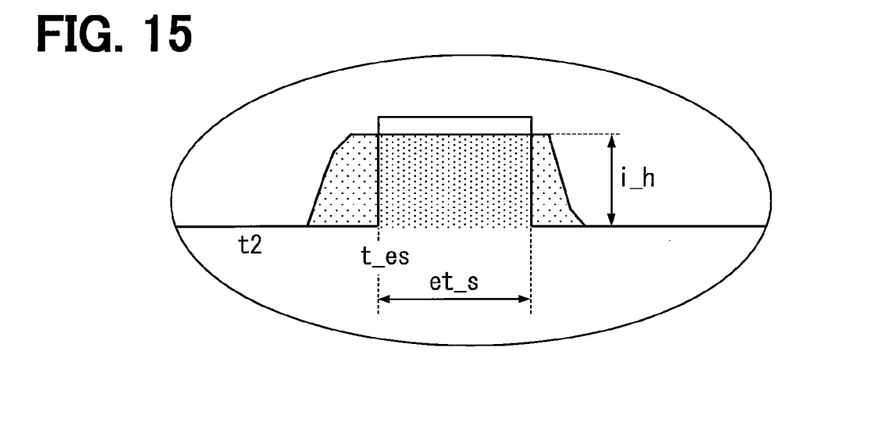
FIG. 15 is a diagram illustrating further another modification of FIG. 8.

Further, as illustrated in FIG. 15, when the apparatus temperature is t2, the maximum i_h of the current value applied to the light emitting diode 16 is controlled to be lower than the maximum current value i_Max (refer to FIG. 6) applied when the apparatus temperature is t1. Also by such a control, the light emission brightness at the start time t_es of the exposure period can be set to about 90% of the maximum brightness. Each of the illumination cover ratios descried in the foregoing embodiments is a conceptual value and may be properly changed according to the specification of the imaging unit and the light projecting unit so as to capture the face image 50 with excellent contrast.

The imaging element of the imaging unit in the foregoing embodiments may properly employ an image sensor such as a CCD (Charge Coupled Device) or a CMOS (Complementary Metal Oxide Semiconductor). The frequency domain of light detected by the imaging element is not limited to the near-infrared domain but may be a visible-light domain. Further, the light emitting diode is desirably to be changed properly in parameters such as the frequency domain of light to be emitted, the number of pieces, and disposition, so as to match the specification of the imaging element.

A shutter for controlling the exposure of the imaging element may be a global shutter which makes all of pixels of the imaging plane enter the exposure state at substantially the same time or may be a rolling shutter which makes the pixels sequentially enter the exposure state from a specific pixel row. Also in a mode of employing such a rolling shutter, the configuration that sets the frame rate in the imaging unit to be large and sets the on-duty ratio of the exposure state to be small can exhibit an effect equivalent to that in the mode of employing the global shutter.

In a modification of the foregoing embodiments, the light emission brightness at the end time t_ef of the exposure period is set to be lower than the light emission brightness at the start time t_es of the period. In the foregoing embodiments, during the period from the start time t_es of the exposure period to the end time t_ef of the exposure period, the current value which determines the light emission brightness shifts constant after it becomes maximum. However, the current value may slightly fluctuate in the exposure period and go below, for example, the current value at the start time t_es of the exposure period.

In the foregoing embodiments, the mounting positions of the imaging unit 10 and the state monitoring apparatus 100 which are on the top face of the steering column 81 may be properly changed as long as the predetermined area PA can be imaged. The state monitoring apparatus may be mounted, for example, on the top face of an instrument panel or attached in a ceiling part adjacent to a sun visor. Further, the imaging unit may be a member separate from the body of the state monitoring apparatus and provided in a position suitable for imaging the predetermined area PA.

A method of determining the predetermined area PA in the foregoing embodiments may be properly changed. For example, the predetermined area PA may be specified so as to include 95 percentile of the eyelips. Further, the method of determining the predetermined area PA is not limited to the method of determining the area by eyelips. For example, making a plurality of drivers of different races, sexes, and ages actually seated on the driver's seat may determine the predetermined area PA. It is desirable to specify such a predetermined area PA on assumption of shift of the face accompanying driving operation.

In the foregoing embodiments, a plurality of functions provided by the control circuit 20 executing the state monitoring program may be provided by hardware or software different from the above-described control apparatuses or combination of them. For example, an analog circuit having a predetermined function without using the program may provide a function corresponding to each of the functional blocks and sub functional blocks.

The foregoing embodiments provide examples of applying the present disclosure to the state monitoring apparatus which is mounted in a vehicle and monitors the state of the driver of the vehicle. In contrast, the present disclosure can be applied not only to a so-called driver status monitor for a car as a vehicle but also to a state monitoring apparatus for monitoring the state of the manipulator of each of various mobile bodies (transport machines) such as a two-wheel vehicle, a three-wheel vehicle, a marine vessel, and an aircraft.

While the present disclosure has been described with reference to embodiments thereof, it is to be understood that the disclosure is not limited to the embodiments and constructions. The present disclosure is intended to cover various modification and equivalent arrangements. In addition, while the various combinations and configurations, other combinations and configurations, including more, less or only a single element, are also within the spirit and scope of the present disclosure.

The invention claimed is:

1. A state monitoring apparatus mounted to a vehicle manipulated by a manipulator to monitor a state of the manipulator by using a face image obtained by imaging a face of the manipulator, comprising:
    an imaging unit generating the face image by receiving light incident from a predetermined area which is preliminarily specified as an area in which the face of the manipulator is positioned;
    an imaging control section adjusting a gradation value of the face image by changing length of an exposure period in which the imaging unit is set in an exposure state;
    a light emitting unit continuously emitting illumination light toward the predetermined area in the exposure period which is set by the imaging control section; and
    a light emission control section controlling the light emitting unit to cause a light emission brightness at a start time of the exposure period to become higher as the exposure period is shortened by the imaging control section, wherein
    the light emission control section
        makes a start time of a light emission period, in which the light emitting unit is set in a light emission state, precede the start time of the exposure period, and
        makes a precedence period, in which the start time of the light emission period precedes the start time of the exposure period, longer as the exposure period is shortened.

2. The state monitoring apparatus according to claim 1, wherein
    the light emission brightness of the light emitting unit at an end time of the exposure period is equal to or higher than the light emission brightness at the start time of the exposure period.

3. The state monitoring apparatus according to claim 1, wherein
    the light emission brightness of the light emitting unit is maintained to be equal to or higher than the light emission brightness at the start time of the exposure period from the start time of the exposure period to the end time.

4. The state monitoring apparatus according to claim 1, wherein
    the light emission control section shortens a transition period of making a light emission of the light emitting unit shift from an off state to an on state as the exposure period is shortened.

5. The state monitoring apparatus according to claim 1, further comprising
    a temperature detecting unit detecting an apparatus temperature of the state monitoring apparatus,
    wherein the light emission control section controls the light emitting unit to cause the light emission brightness at the start time of the exposure period to become lower as the apparatus temperature detected by the temperature detecting unit increases.

6. A non-transitory computer readable storage medium comprising instructions for execution by a computer, the instructions including a state monitoring method being computer-implemented for causing a computer mounted to a vehicle manipulated by a manipulator to monitor a state of the manipulator by using a face image obtained by imaging a face of the manipulator,
    the method comprising:
    generating the face image by receiving light incident from a predetermined area which is preliminarily specified as an area in which the face of the manipulator is positioned;
    adjusting a gradation value of the face image by changing a length of an exposure period, in which an exposure state is set, when generating the face image;
    emitting illumination light continuously toward the predetermined area in the exposure period of which the length is changed when adjusting the gradation value; and
    controlling the emitting of the illumination light with a light emitting unit to cause a light emission brightness at a start time of the exposure period to become higher as the length of the exposure period is changed to be shorter when adjusting the gradation value, wherein
    a start time of a light emission period, in which the light emitting unit is set in a light emission state, is caused to precede the start time of the exposure period, while a precedence period, in which the start time of the light emission period precedes the start time of the exposure period, is caused to be longer as the exposure period is shortened.

7. A state monitoring apparatus mounted to a vehicle manipulated by a manipulator to monitor a state of the manipulator by using a face image obtained by imaging a face of the manipulator, comprising:
    an imaging unit generating the face image by receiving light incident from a predetermined area which is preliminarily specified as an area in which the face of the manipulator is positioned;
    an imaging control section adjusting a gradation value of the face image by changing length of an exposure period in which the imaging unit is set in an exposure state;
    a light emitting unit continuously emitting illumination light toward the predetermined area in the exposure period which is set by the imaging control section; and
    a light emission control section controlling the light emitting unit to cause a light emission brightness at an end time of the exposure period to become closer to a predetermined light emission brightness as the exposure period is caused to become shorter by the imaging control section.

8. A state monitoring apparatus mounted to a vehicle manipulated by a manipulator to monitor a state of the manipulator by using a face image obtained by imaging a face of the manipulator, comprising:

an imaging unit generating the face image by receiving light incident from a predetermined area which is preliminarily specified as an area in which the face of the manipulator is positioned;

an imaging control section adjusting a gradation value of the face image by changing length of an exposure period in which the imaging unit is set in an exposure state;

a light emitting unit continuously emitting illumination light toward the predetermined area in the exposure period which is set by the imaging control section; and a light emission control section controlling the light emitting unit to cause a light emission brightness at a start time of the exposure period to become higher as the exposure period is shortened by the imaging control section, wherein the light emission control section shortens a transition period of making a light emission of the light emitting unit shift from an off state to an on state as the exposure period is shortened.

9. A state monitoring apparatus mounted to a vehicle manipulated by a manipulator to monitor a state of the manipulator by using a face image obtained by imaging a face of the manipulator, comprising:

an imaging unit generating the face image by receiving light incident from a predetermined area which is preliminarily specified as an area in which the face of the manipulator is positioned;

an imaging control section adjusting a gradation value of the face image by changing a length of an exposure period in which the imaging unit is set in an exposure state;

a light emitting unit continuously emitting illumination light toward the predetermined area in the exposure period which is set by the imaging control section; and a light emission control section controlling the light emitting unit to cause a light emission brightness at a start time of the exposure period to become closer to a predetermined light emission brightness as the exposure period is caused to become shorter by the imaging control section.

10. The state monitoring apparatus according to claim 9, wherein the predetermined light emission is maintained to be unchanged regardless of whether the length of the exposure period is changed.

11. The state monitoring apparatus according to claim 9, wherein the light emission control section makes a start time of a light emission period, in which the light emitting unit is set in a light emission state, precede the start time of the exposure period, and makes a precedence period, in which the start time of the light emission period precedes the start time of the exposure period, longer as the exposure period is shortened.

12. The state monitoring apparatus according to claim 9, wherein the light emission brightness of the light emitting unit at an end time of the exposure period is equal to or higher than the light emission brightness at the start time of the exposure period.

13. The state monitoring apparatus according to claim 9, wherein the light emission brightness of the light emitting unit is maintained to be equal to or higher than the light emission brightness at the start time of the exposure period from the start time of the exposure period to the end time.

14. The state monitoring apparatus according to claim 9, wherein the light emission control section shortens a transition period of making a light emission of the light emitting unit shift from an off state to an on state as the exposure period is shortened.

15. The state monitoring apparatus according to claim 9, further comprising a temperature detecting unit detecting an apparatus temperature of the state monitoring apparatus, wherein the light emission control section controls the light emitting unit to cause the light emission brightness at the start time of the exposure period to become lower as the apparatus temperature detected by the temperature detecting unit increases.

16. A state monitoring apparatus mounted to a vehicle manipulated by a manipulator to monitor a state of the manipulator by using a face image obtained by imaging a face of the manipulator, comprising:

an imaging unit generating the face image by receiving light incident from a predetermined area which is preliminarily specified as an area in which the face of the manipulator is positioned;

an imaging control section adjusting a gradation value of the face image by changing length of a continued exposure period in which the imaging unit is set continuously in an exposure state;

a light emitting unit continuously emitting illumination light toward the predetermined area in the continued exposure period which is set by the imaging control section; and a light emission control section controlling the light emitting unit to cause a light emission brightness at a start time of the continued exposure period to become higher as the continued exposure period is caused to become shorter by the imaging control section such that when the continued exposure period is changed from a first continued exposure period into a second continued exposure period that is shorter than the first continued exposure period, the light emission brightness is caused to become higher from a first light emission brightness at a start time of the first continued exposure period to a second light emission brightness at a start time of the second continued exposure period.

17. The state monitoring apparatus according to claim 16, wherein the light emission control section makes a start time of a light emission period, in which the light emitting unit is set in a light emission state, precede the start time of the continued exposure period, and makes a precedence period, in which the start time of the light emission period precedes the start time of the continued exposure period, longer as the continued exposure period is shortened.

18. The state monitoring apparatus according to claim 16, wherein the light emission brightness of the light emitting unit at an end time of the continued exposure period is equal to or higher than the light emission brightness at the start time of the continued exposure period.

19. The state monitoring apparatus according to claim 16, wherein the light emission brightness of the light emitting unit is maintained to be equal to or higher than the light emission brightness at the start time of the continued exposure period from the start time of the continued exposure period to the end time.

20. The state monitoring apparatus according to claim 16, wherein
the light emission control section shortens a transition period of making a light emission of the light emitting unit shift from an off state to an on state as the continued exposure period is shortened.

* * * * *